United States Patent [19]

Karami

[11] 4,425,129
[45] Jan. 10, 1984

[54] DIAPER WITH CUSHIONED ELASTIC LEG HOLD EDGES
[75] Inventor: Hamzeh Karami, Tilff, Belgium
[73] Assignee: Colgate-Palmolive Company, New York, N.Y.
[21] Appl. No.: 328,295
[22] Filed: Dec. 7, 1981
[51] Int. Cl.³ ............................................. A61F 13/16
[52] U.S. Cl. ................................................. 604/385
[58] Field of Search ................................. 604/385–386
[56] References Cited
U.S. PATENT DOCUMENTS
4,050,462 9/1977 Woon et al. .......................... 604/385
4,212,302 7/1980 Karami ................................. 604/385

4,325,372 4/1982 Teed ..................................... 604/385

Primary Examiner—C. Fred Rosenbaum
Assistant Examiner—Sherri E. Vinyard
Attorney, Agent, or Firm—Norman Blumenkopf; Herbert S. Sylvester; Murray M. Grill

[57] ABSTRACT

A disposable diaper having cushioned elasticized leghold edges formed from elastic members secured between the backing sheet and the absorbent pad or mounted directly in the absorbent pad and adapted to overcome leakage through the leg hold edges while cushioning so as not to make indentations or marks on the infant's skin.

4 Claims, 8 Drawing Figures

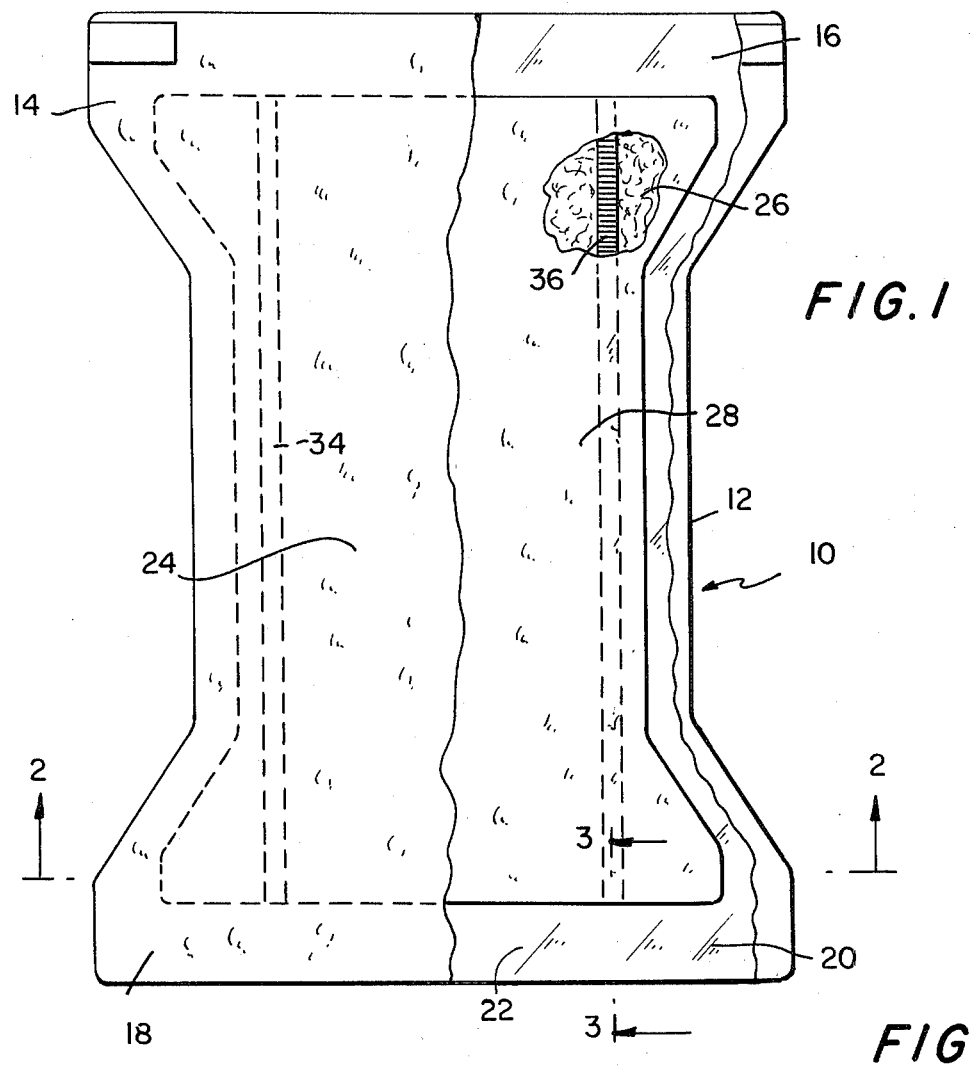
FIG. 1
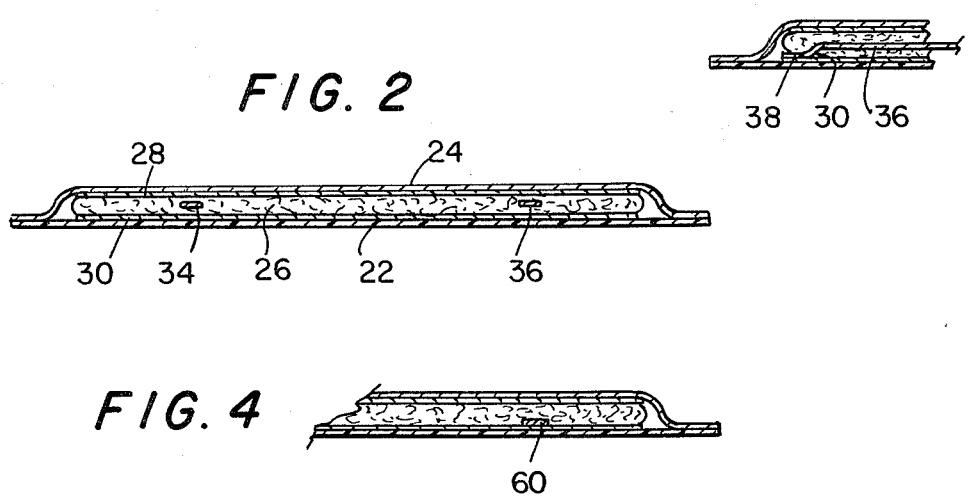
FIG. 2
FIG. 3
FIG. 4

DIAPER WITH CUSHIONED ELASTIC LEG HOLD EDGES

BACKGROUND OF THE INVENTION

1. Field of the Invention

This invention relates to disposable diapers and more particularly to elasticized and contoured diapers.

2. Description of the Prior Art

In the past elasticized contoured diapers have been developed such as that disclosed in the U.S. patent to Buell, U.S. Pat. No. 3,860,003, issued Jan. 14, 1975, for "Contractable Side Portions for Disposable Diaper" wherein elastic strips are secured to the crotch portions of the diaper and spaced at least ¾ inch from the absorbent pad to form elasticized crotch seals for securement over the legs of the infant to prevent loss of fluid from the interior of the diaper along the legs of the infant. The elasticized strips were placed more than ¾ inch from the absorbent pad in order to prevent pleats froming transversely of the crotch area of the diaper.

Another diaper is presently in production in which the elasticized strips are less than ¾ inch from the absorbent pad for the production of the transverse pleats in the crotch area of the diaper for the purpose of increasing the absorbent capacity at the crotch area of the diaper. This diaper is disclosed in U.S. Pat. No. 4,050,462. However, it has been found that these pleats may act as a channel resulting in excessive diaper leakage and the pleats in the crotch area make the infant's bottom uncomfortable when sitting, especially while the diaper is not saturated.

The elasticized construction in both the diapers as disclosed in the aforesaid patents cause marks and indents to be formed in the skin of the infant on which these types of diapers are used.

SUMMARY OF THE INVENTION

The present invention overcomes the disadvantages of both the prior art diapers. The elastic members are placed according to the present invention within the confines of the absorbent pad or between the absorbent pad and the backing sheet cushioning the elastic action and preventing marks and indents being formed in the skin of the infant while providing unexpectedly better protection against excessive leakage through leg hold edges.

The concept of the present invention features a disposable diaper which, in a preferred embodiment, is contoured in an hour-glass configuration and has an absorbent body between a top sheet and a backing sheet with elastic members secured between the backing sheet and the absorbent pad or disposed completely within the confines of the absorbent pad.

BRIEF DESCRIPTION OF THE DRAWINGS

FIG. 1 is a plan view of a diaper constructed in accordance with the concepts of the present invention;

FIG. 2 is a transverse sectional view taken along the plan of line 2—2 in FIG. 1 through the crotch portion of the diaper;

FIG. 3 is a sectional detail view taken along the plane of line 3—3 in FIG. 1;

FIG. 4 is a partial view similar to FIG. 2, but showing a modification of the invention;

DETAILED DESCRIPTION OF THE INVENTION

Figure 5:
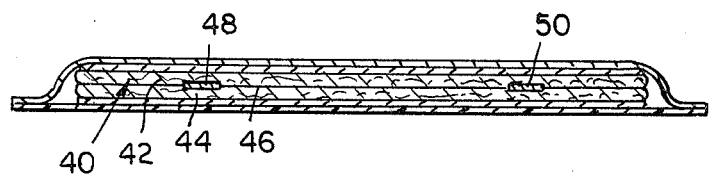
FIG. 5 is a partial view of another modification of the invention.

With continuing reference to the accompanying drawing, wherein like reference numerals designate similar parts throughout the various views, reference numeral 10 generally designates an elasticized and contoured disposable diaper constructed in accordance with the concepts of the present invention. The diaper is of an hour-glass configuration having a crotch area 12 and four portions of greater width defining ears 14, 16, 18, and 20. The diaper includes a backing sheet 22 of an impervious material, such as polyethylene or polypropylene film. A top sheet 24, preferably of a typical non-woven bonded (e.g. by resin latex) rayon or rayon-polyester fiber sheet or a spunbonded sheet of polyethylene or polypropylene fibers, is sealed, preferably by hot melt lines, to the backing sheet along the peripheral edges of the diaper. An absorbent pad 26 is disposed between the top sheet 24 and the backing sheet 22 and may be of conventional wood fluff (e.g. from chemical, semi-chemical or thermo-mechanical pulp) or the like or a plurality of creped sheets as shown in U.S. Pat. No. Re. 26,151. An upper waddin- sheet 28 and a lower wadding sheet 30 are provided, the pad and the wadding sheets conforming generally in contours to the hour-glass shape.

A pair of elasticized strips 34 and 36 which may be provided with adhesive on at least the bottom end surfaces thereof are disposed wholly within the wood fluff or creped sheets of the pad 26 and may be bonded at the ends as at 38, FIG. 3, with the adhesive to the lower wadding sheet 30 inwardly of the edges of the pad 26 or, in the case of creped sheets, for the pad 26, the strips 34 and 36 may be secured with adhesive spots to one or more sheets in the inner region of the pad 26. The adhesive may be any conventional hot melt or pressure-sensitive adhesive and, preferably, one that, at ambient temperatures is flexible and extensible (i.e. elastic-like) in nature. The strips 34 and 36 preferably extend the entire length of the pad inwardly of the ears 12, 14, 16, 18 so that the tension provided by the elasticized strips is such that the pad 26 itself cushions the leg hold edges to form especially fluid tight seals without causing marks or indents to be formed on an infant's skin. The top and bottom wadding sheets may be the conventional paper or tissue heretofore used in the art (i.e. cellulosic fibers) or may be formed of hydrophobic fibers (e.g. polyester, polyethylene or polypropylene) or rendered hydrophobic by suitable and conventional treatments (e.g. resins).

In FIG. 4 there is shown a variation wherein the entire elasticized strip 60 is bonded to either the lower wadding sheet 30 or the backing sheet 22 or both below the pad 26 between the pad 26 and the backing sheet 22 so that the strips 60 cause the pad 26 to cushion the leg hold edges.

The elastic strips 34 and 36 and 60 may be varied in widths but generally from about 3 to 12 mm with a range of about 5 to 8 mm being preferred. The adhesive width used in bonding strips may be somewhat greater or lesser than that of the elastic strips and typically, for a 6 mm elastic strip, would range from about 4 to 12 mm. Typical thicknesses of strips 34 and 36 range from a few mils (e.g. 1 to 5) to 15 or 20 mm, with the higher ranges more general for foams.

The elastic strips 34 and 36 may be of any suitable construction and materials such as the conventional rubberized (or otherwise elastomerized) fibers or may be simply a strip of elastomeric resin or foamed resin which may or may not be provided with adhesive. Such strips are generally available as double-sided transfer tapes (e.g. 3M Co., St. Paul, Minn., tape No. 465 high tack pressure-sensitive tape).

The backing sheet 22 and/or the top sheet 24 may be fully elasticized and provided with a waist band if desired. A suitable elastic backing sheet material id disclosed in U.S. Pat. No. 4,166,464. Such a sheet provided with apertures provides an acceptable top sheet. Such apertures may vary from about 0.1 mm to about 10 mm or more in diameter and may comprise from 5% to about 80% of the total surface of the top sheet, particularly in the fluid contacting region.

In FIG. 5 there is shown a variation wherein the absorbent pad 40 is comprised of two separate pads 42 and 44 separated by a wadding tissue or sheet or nonwoven sheet 46 and the elasticized strips 48 and 50 are bonded to the upper surfaces thereof as shown. If desired, the strips 48 and 50 may be bonded to the lower surfaces of sheet 46. Bonding may be by means of suitable continuing line or spots of adhesive.

Figure 7:
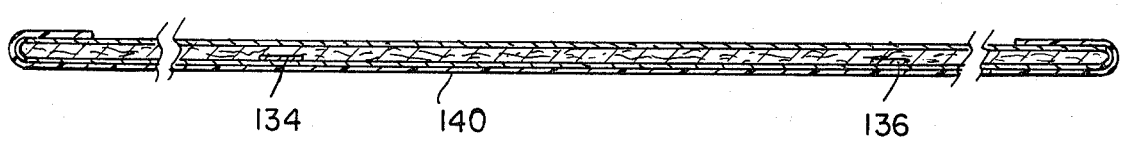
FIG. 7 is a vertical sectional view of the box-pleated diaper in an unfolded state; and, FIG. 8 is a vertical sectional view of a box-pleated diaper according to the invention employing two pads.
Figure 6:
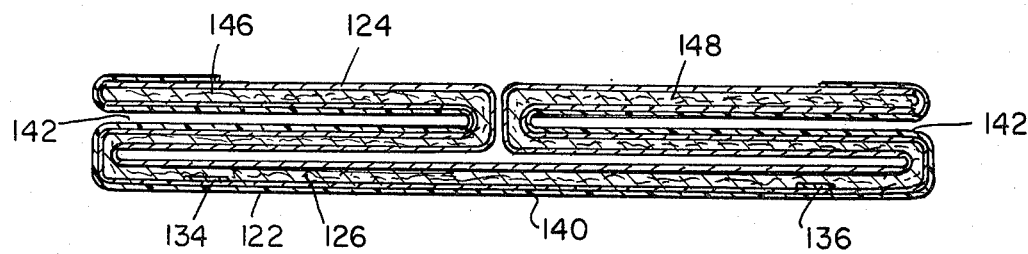
FIG. 6 is a vertical sectional view of an embodiment of the invention in a box-pleated diaper.

With reference to FIGS. 6 and 7, herein is shown a box-pleated diaper having a backing sheet 122 of an impervious material. A top sheet 124 of typically nonwoven fibers is sealed to the backing sheet along the peripheral edges of the diaper. An absorbent pad 126 is disposed between the top sheet 124 and the backing sheet 122. A pair of elasticized strips 134 and 136 are disposed between the backing sheet 122 and the pad 126 and held by adhesive at its ends to the edges of the diaper. The diaper is folded in a box-pleated configuration having a central portion 140, two inwardly extending panels 142 and 144, and two outwardly extending panels 146 and 148.

Figure 8:
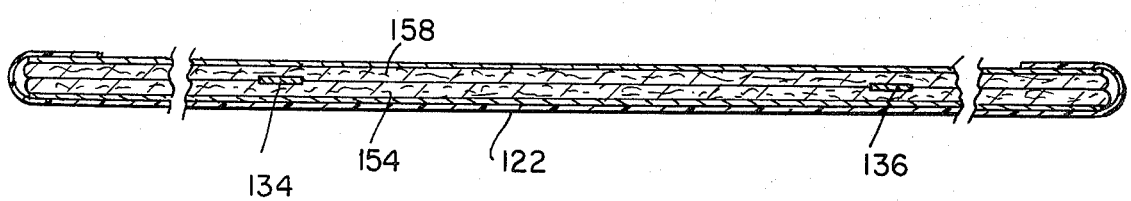

In FIG. 8 there is shown a further modification where in lieu of the absorbent pad 126, two pads 156 and 158 are employed with the elastic strips 134 and 136 therebetween held by friction between the pads. The strips may be sealed at the opposite peripheral edges to the top sheet or backing sheet or therebetween. The same means sealing the top sheet to the backing sheet may be used to secure and seal the ends of the elasticized strips 134 and 136 to the backing sheet 122 and may be adhesive or hot melt lines.

I claim:

1. A disposable diaper comprising a backing sheet, a pair of absorbent pads on said backing sheet, a top sheet overlying said absorbent pads, means securing said top sheet to said backing sheet with said pads therebetween, and elasticized strips disposed between said pads.

2. A disposable diaper according to claim 1, wherein the means sealing said top sheet to said backing sheet secures the ends of said elasticized strips to said backing sheet.

3. A diaper according to claim 2, wherein said diaper is box-pleated.

4. A diaper according to claim 2, wherein said absorbent pads are of hour-glass configuration.

* * * * *